US 9,494,593 B2

United States Patent
Chang et al.

(10) Patent No.: US 9,494,593 B2
(45) Date of Patent: Nov. 15, 2016

(54) METHOD FOR SEPARATING NANOPARTICLES WITH A CONTROLLED NUMBER OF ACTIVE GROUPS

(75) Inventors: Walter Hong-Shong Chang, Tao-Yuan (TW); Jimmy Kuan-Jung Li, Taipei (TW); Ralph Alexander Sperling, Eltville (DE); Teresa Pellegrino, Lecce (IT); Wolfgang Parak, Munich (DE)

(73) Assignee: CHUNG YUAN CHRISTIAN UNIVERSITY, Tao-Yuan County (TW)

( * ) Notice: Subject to any disclaimer, the term of this patent is extended or adjusted under 35 U.S.C. 154(b) by 2349 days.

(21) Appl. No.: 11/302,240

(22) Filed: Dec. 14, 2005

(65) Prior Publication Data
US 2007/0134679 A1 Jun. 14, 2007

(51) Int. Cl.
*G01N 33/543* (2006.01)
*G01N 33/58* (2006.01)

(52) U.S. Cl.
CPC .................................. *G01N 33/587* (2013.01)

(58) Field of Classification Search
CPC .................................................. G01B 33/587
USPC ......... 436/526, 518, 525, 545; 435/969, 7.1, 435/7.5
See application file for complete search history.

(56) References Cited

U.S. PATENT DOCUMENTS

2003/0185890 A1* 10/2003 Zuckermann et al. ....... 424/484
2005/0130167 A1* 6/2005 Bao et al. ........................ 435/6

OTHER PUBLICATIONS

Parak et al. "Biological Applicatioins of Colloidal Nanocrystals". Nanotechnology 14, 2003, R15-R27.*

* cited by examiner

*Primary Examiner* — Mark Shibuya
*Assistant Examiner* — Pensee Do
(74) *Attorney, Agent, or Firm* — WPAT, PC; Justin King

(57) ABSTRACT

The present invention discloses a method for separating nanoparticles with a controlled number of active groups is disclosed. First, a plurality of nanoparticles are provided, wherein the surface of the nanoparticle comprises a plurality of first active groups. Next, a plurality of functional ligands are provided, wherein the functional ligand comprises at least one second active group and at least one third active group. Then, a binding process is performed to bind the nanoparticle with the functional ligand, wherein the first active group connects with the second active group. After the binding process, a separation process is performed to isolate a plurality of nanoparticles with a controlled number of the third active groups. The controlled number is integers from 0 to 10.

17 Claims, 7 Drawing Sheets

METHOD FOR SEPARATING NANOPARTICLES WITH A CONTROLLED NUMBER OF ACTIVE GROUPS

BACKGROUND OF THE INVENTION

1. Field of the Invention

The present invention is generally related to a method for separating nanoparticles, and more particularly to a method for separating nanoparticles with a controlled number of active groups.

2. Description of the Prior Art

Nanoparticle labels with a discrete and controlled number of attached ligands (or even more general: functional groups) would be very desirable. Dependent on material, size, and shape, nanoparticles can have different functionalities, such as fluorescence, phosphorescence, optical absorption, or magnetic moment, and can thus be detected with different techniques. Ligand molecules attached to the surface of such nanoparticles will specifically bind to their corresponding receptors. Such constructs, as for instance gold or semiconductor nanoparticles decorated with oligonucleotides, streptavidin or antibodies, have been successfully used in life sciences to trace the position of single proteins within the membrane of living cells, and to visualize the structure of artificially created nanostructures.

One key issue for some of the above-mentioned applications is the ability to control the number of ligand molecules bound to each nanoparticle. By exactly controlling the number of binding sites per nanoparticle unwanted cross-linking effects between the labels or between the structures to be labeled, which eventually can lead to agglomeration, can be avoided. For the controlled assembly of nanoparticle groupings such defined building blocks are a prerequisite. Except few cases, so far it has not been possible to directly synthesize such nanoparticles. Therefore, new method for separating nanoparticles with a controlled number of active groups is still needed corresponding to both economic effect and utilization in industry.

SUMMARY OF THE INVENTION

In accordance with the present invention, new method for separating nanoparticles with a controlled number of active groups is provided.

One object of the present invention is to employ functional ligands, wherein the functional ligand can have at least one binding group and at least one active group. If the functional ligand(s) bound to a nanoparticle by the binding group change its overall effective size sufficiently enough, fractions of nanoparticles with a different number of functional ligands can be then separated. Therefore, nanoparticles with a controlled number of the active groups can be sorted out.

Another object of the present invention is to render hydrophobic nanoparticles hydrophilic before the binding process, such as: coating by amphiphilic polymers (alternating or block-copolymers) or lipids, so as to synthesize nanoparticles of different materials (such as fluorescent or magnetic ones) that have an identical surface. For this reason also the concept of the attachment of functional ligands per nanoparticle is not restricted to one type of nanoparticles but should be applicable for nanoparticles of most materials. Therefore, this present invention does have the economic advantages for industrial applications.

Accordingly, the present invention discloses a method for separating nanoparticles with a controlled number of active groups. First, a plurality of nanoparticles are provided, wherein the surface of the nanoparticle comprises a plurality of first active groups. Next, a plurality of functional ligands are provided, wherein the functional ligand comprises at least one second active group and at least one third active group. Then, a binding process is performed to bind the nanoparticle with the functional ligand, wherein the first active group connects with the second active group. After the binding process, a separation process is performed to isolate a plurality of nanoparticles with a controlled number of the third active groups. The controlled number is integers from 0 to 10.

DESCRIPTION OF THE PREFERRED EMBODIMENTS

What probed into the invention is a method for separating nanoparticles with a controlled number of active groups. Detailed descriptions of the production, structure and elements will be provided in the following in order to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

Definitions

The term "conjugate" herein refers to nanoparticle bound with functional ligand(s).

The term "nanoparticle" can be made of organic, inorganic or metal material, and more preferred refers to metal and metal oxide nanoparticles or semiconductor nanocrystals. "Semiconductor nanocrystals" herein is used synonymously with the term colloidal "quantum dot" as commonly understood and herein refers to nanocrystals that are composed of a semiconducting material, such as: IIA-VIA semiconductors, IIA-VA semiconductors, IVA-IVA semiconductors, and IVA-VIA semiconductors, and are made in such a way as to crystallize in exceedingly small sizes, e.g. from 2-20 nm in diameter. The semiconductor nanocrystals used herein are colloidal, which refers to the fact that the semiconductor nanocrystals are dispersed within a continuous medium in a manner that prevents them from being filtered easily or settled rapidly. The semiconductor nanocrystals used herein luminesce or upon excitation by a light source. The semiconductor nanocrystals used herein preferably are modified to be hydrophilic and may be further modified to contain chemical functional groups, cross-linkers, biological molecules and combinations thereof.

The term, "biological molecule" herein refers to molecules including, by way of example only, such classes of substances as monoclonal and polyclonal antibodies, nucleic acids (both monomeric and oligomeric), proteins, enzymes, lipids, polysaccharides, sugars, peptides, polypeptides, drugs, and bioligands.

The term "connect" herein refers to describe the relationship between the first active group and the second active group, or between the third active group and the fourth active group. For example, the first active group is connected to said second active group through chemical or physical interaction (e.g. covalent bond, coordination bond, van der Waals force, hydrogen bond, etc.).

Figure 1:
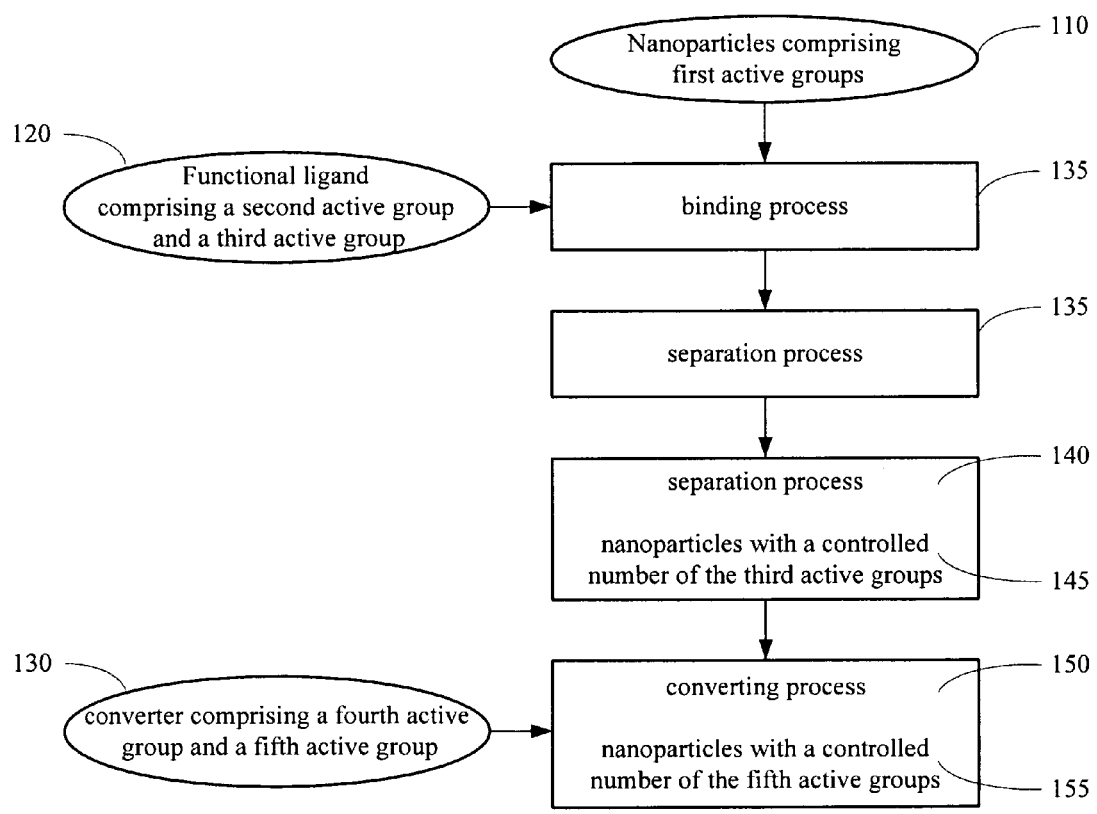
FIG. 1 is a flow chart of a method for separating nanoparticles with a controlled number of active groups in accordance with the first embodiment of the present invention.
Figure 2A:
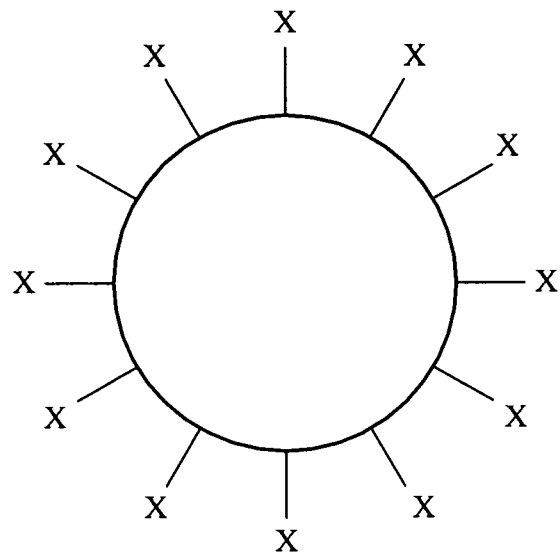
FIG. 2A to 2B show the preferred constructs of the nanoparticles.
Figure 2B:
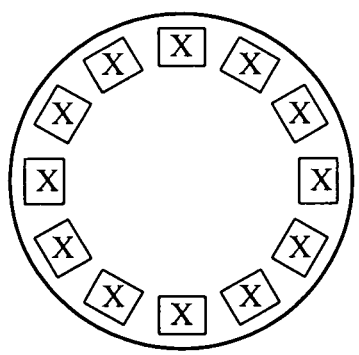

Referring to FIG. 1, in a first embodiment of the present invention, a method for separating nanoparticles with a controlled number of active groups is disclosed. First, a plurality of nanoparticles 110 are provided, wherein the surface of the nanoparticle 110 comprises a plurality of first active groups. The preferred diameter of the nanoparticle 110 is smaller than 50 nm, and the nanoparticle 110 comprises one of the following group: quantum dot (e.g., CdS, CdSe, CdTe, ZnSe, ZnS, PbS, PbSe, and their alloys), metallic nanoparticle (e.g., gold, silver, copper, titanium, nickel, platinum, palladium, cobalt, and their alloys), metal oxide nanoparticle, doped metal oxide particles, metalloid and metalloid oxide nanoparticles, the lanthanide series metal nanoparticles, and combinations thereof. Furthermore, there are two preferred constructs of the nanoparticles 110: a) as shown in FIG. 2A, the nanoparticle 110 has the first active groups X thereon; b) as shown in FIG. 2B, the nanoparticle 110 is bound with the first active groups X. For example, the surface of the nanoparticle 110 is modified to be bound with the first active group by an amphiphilic oligomer or polymer. Next, a plurality of functional ligands 120 are provided, wherein the functional ligand 120 comprises at least one second active group and at least one third active group. Then, a binding process 135 is performed to bind the nanoparticle 110 with the functional ligand 120, wherein the first active group connects with the second active group through chemical bonding or physical bonding. Finally, a separation process 140 is performed to isolate a plurality of nanoparticles with a controlled number of the third active groups 145, wherein the controlled number is integers from 0 to 10.

Furthermore, the preferred molecular weight of the functional ligand is larger than or equal to 1000 g/mol, and the separation process comprises size exclusion chromatography (SEC) and gel electrophoresis, wherein SEC comprises Gel Chromatography. However, for nanoparticles with different size, different separation methods, different operational parameters (e.g. temperature, gel species), or different functional ligands, the molecular weight limit of the functional ligand might be varied. In a preferred example of this embodiment, 3000 g/mol is a better lower limit for the separation process.

Figure 3A:
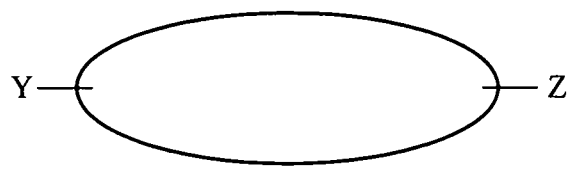
FIG. 3A to 3C show the preferred constructs of the functional ligands.
Figure 3B:
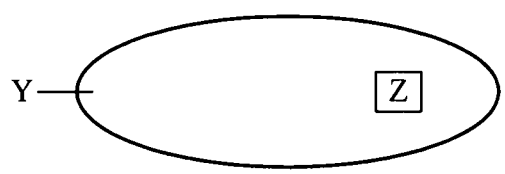
Figure 3C:
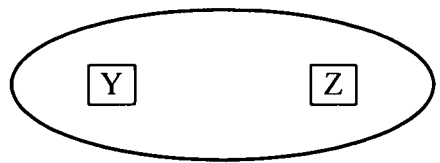

In this embodiment, three preferred constructs of the functional ligand 120 are illustrated: a) as shown in FIG. 3A, the functional ligand 120 comprises a spacer bound with the second active group Y and the third active group Z, wherein the spacer comprises oligomer or polymer; b) as shown in FIG. 3B, the functional ligand 120 comprises a spacer having the third active group Z therein, and bound with the second active group Y, wherein the spacer comprises biological molecule except nucleic acids; c) as shown in FIG. 3C, the functional ligand 120 comprises a spacer having the second active group Y and the third active group Z therein, wherein the spacer comprises biological molecule except nucleic acids. Furthermore, the mentioned oligomer or polymer of the functional ligand in construct a) comprises any one or any combination of the group consisting of: polyol [e.g., polyethylene glycol, polypropylene glycol, polytetramethylene glycol, poly(oxyethylene) glycol, poly(oxypropylene) poly(oxyethylene) triol, polycarbonate glyco], acrylate based oligomer or polymer, vinyl based oligomer or polymer.

Additionally, the mentioned first active groups, the second active group, and the third active group are independently selected from the group consisting of:

a) chemical functional group, such as: sulfonic group, hydroxyl group, amino group, sulfhydryl group, carboxyl group, epoxy group, isocyanate group, organic halide group, maleimidyl group, alkoxy group, succinimidyl group, ortho-pyridylthiolic group, ortho-pyridyldisulfidyl group, vinylsulfonic group, acrylate group, alkyl ketone group, hydrazine group, hydrazide group, thioester group, and aldehydyl group.

b) biological molecule as described in definitions c) protecting group, such as: Fmoc group, Boc group Moreover, it is noteworthy that "biological molecule" can be used as one kind of active group or one kind of functional ligand. The major difference is molecular weight, wherein the MW of biological molecule as active groups is smaller than that of biological molecule as functional ligand. For example, "small biological molecules" comprises biotin, cystein, benzylguanine, peptides, small aptamers (DNA oligomers, RNA oligomers, PNA oligomers), etc. On the other hand, "big biological molecules" comprises antibodies, aptamers, avidin, neutravidin, stepavidin, etc.

In this embodiment, a converting process 150 can be performed after the separation process 140, so as to convert the third active group of the nanoparticle into a fifth active group. One example of the converting process 150 comprises: (1) providing a plurality of converters 130, wherein the converter 130 comprises a fourth active group and at least one fifth active group, such as: NHS-PEG-biotin; (2) connecting the third active group of the nanoparticle 110 with the fourth active group, so as to form a plurality of nanoparticles with a controlled number of the fifth active groups 155. The fourth active group and the fifth active group are independently selected from the group consisting of:

a) chemical functional group, such as: sulfonic group, hydroxyl group, amino group, sulfhydryl group, carboxyl group, epoxy group, isocyanate group, organic halide group, maleimidyl group, alkoxy group, succinimidyl group, ortho-pyridylthiolic group, ortho-pyridyldisulfidyl group, vinylsulfonic group, acrylate group, alkyl ketone group, hydrazine group, hydrazide group, thioester group, and aldehydyl group.

b) biological molecule as described in definitions c) protecting group, such as: Fmoc group, Boc group Another example of the converting process 150 comprises a redox reaction to reduce or oxidize the third active group to the fifth active group. Still another example of the converting process 150 comprises a deprotecting reaction. For a preferred case, the third active group is Fmoc-protected or Boc-protected amino group, and piperidine or TFA can be used as deprotecting agent respectively.

In this embodiment, the functional ligand can further comprise at least one cleaving site between said second active group and said third active group. Therefore, after the completion of the separation process, a cleaving process is performed to break said cleaving site. Then, there are two kinds of results: a) the cleaving site is broken to form a sixth active group; b) the functional ligand originally comprises a seventh active group between said second active group and said cleaving site, and the seventh active group remains bound to the nanoparticle after the cleavage. In this way, also the same exact number of a shorter functional ligand bound to the nanoparticle can be obtained. Additionally, some preferred examples are listed as following: when the cleaving site is disulfide bond, the cleaving process uses a reduction agent as cleaving agent, such as: dithiothreitol (DTT), tris(2-carboxyethyl)phosphine hydrochloride (TCEP); when the cleaving site is peptide or protein, the cleaving process uses trypsin as cleaving agent; when the cleaving site is peptide or protein or DNA or RNA or PNA, the cleaving process uses enzymes as cleaving agent.

Example 1

High quality inorganic nanoparticles of many materials with excellent size distribution, which have been synthesized in organic solvents, can be transferred to aqueous solution by embedding them in an amphiphilic polymer shell. (see FIG. 1a) (reference 1: Wu, M. X.; Liu, H.; Liu, J.; Haley, K. N.; Treadway, J. A.; Larson, J. P.; Ge, N.; Peale, F.; Bruchez, M. P. Nature Biotechnology 2003, 21, 452) (reference 2: Pellegrino, T.; Manna, L.; Kudera, S.; Liedl, T.; Koktysh, D.; Rogach, A. L.; Keller, S.; Rädler, J.; Natile, G.; Parak, W. J. Nanoletters 2004, 4, (4), 703-707) This process yields nanoparticles with an excellent size distribution (i.e. the size distribution does not get significantly worse due to the polymer shell) that yield narrow bands in gel electrophoresis.

By covalently attaching mono- or bifunctional short polyethylene glycol (PEG) functional ligands to this polymer shell, the size of the nanoparticles increased with the number and the molecular weight of the attached molecules. The binding can thus be monitored by gel electrophoresis [(a)-(h) of FIG. 4). This approach results in stable water-soluble nanoparticles of different materials with identical surface chemistry and many functional groups on their outside (e.g. —$NH_2$ on the end of the PEG which is pointing towards solution). The covalent linkage of (biological) molecules to the surface of such nanoparticles has been demonstrated by using crosslinker. PEG functional ligands on the nanoparticle surface simplify the bioconjugation of nanoparticles. Nanoparticles are typically stabilized in aqueous solution by electrostatic repulsion. Since also many biological molecules are charged, repulsive interactions between the molecule and the nanoparticle (for likewise charged nanoparticles and molecules) or electrostatic adsorption (for oppositely charged nanoparticles and molecules) can occur. In order to suppress unwanted repulsive charge interactions salt can be added to screen the charge of the nanoparticles and molecules. However, this eventually leads to an agglomeration of the nanoparticles, which do not repel each other anymore with sufficient force. On the other hand, nanoparticles modified with PEG on their surface repel each other by steric interaction and the bioconjugation can be performed at higher salt concentrations. In this way PEG reduces the risk of nanoparticle agglomeration and enhanced the binding yield.

Example 2

Amino-modified PEG bearing an amino group only on one end of the PEG chain (hereinafter as $NH_2$—PEG, regardless of the unmodified end thereof) has been attached to the —COOH groups of the surface of polymer-coated Au nanoparticles with standard bioconjugation chemistry using 1-Ethyl-3-(3-Dimethylaminopropyl) carbodiimide Hydrochloride (EDC). The more $NH_2$—PEG functional ligands are bound per Au nanoparticle the bigger the resulting conjugate becomes. This can be easily observed using gel-electrophoresis: Negatively charged polymer-coated Au nanoparticles migrate towards the positive pole and they become the more retarded the more $NH_2$—PEG functional ligands has been attached [see (a) and (b) of FIG. 4]. If $NH_2$—PEG functional ligand with a molecular weight 5000 g/mol is used discrete bands can be observed [see (c) and (d) of FIG. 4]. In analogy to the well known DNA/Au-nanoparticle conjugates we ascribe these bands to Au-nanoparticles with no, exactly one, exactly two, etc. $NH_2$—PEG functional ligands attached per nanoparticle. To test this assumption we performed the same control experiments as have been used in the case of DNA/Au-nanoparticle conjugates (as performed by the Alivisatos group) as will be described below. In order to introduce functional groups as anchor points for further attachment of biological molecules, PEG functional ligand with two modified ends are used. PEG modified with amino groups at both ends (hereinafter as $NH_2$—PEG-$NH_2$) is covalently attached to the surface of polymer-coated Au nanoparticles using EDC as described above. The appropriate choice of the concentrations prevented inter-particle crosslinking. This is confirmed by comparing the migration of Au-nanoparticles modified under the same conditions with $NH_2$—PEG and $NH_2$—PEG-$NH_2$ with gel electrophoresis [see (e)-(h) of FIG. 4]. Nanoparticles modified with $H_2$—PEG-$NH_2$ exhibit free amino groups on their surface so that molecules bearing a N-hydroxysuccinimide ester (NHS) functionality can be directly attached via the formation of a covalent bond. We demonstrated this for the case of NHS-PEG-biotin resulting in biotin-modified nanoparticles. In the following the key experiments are described in more detail.

Figure 4:
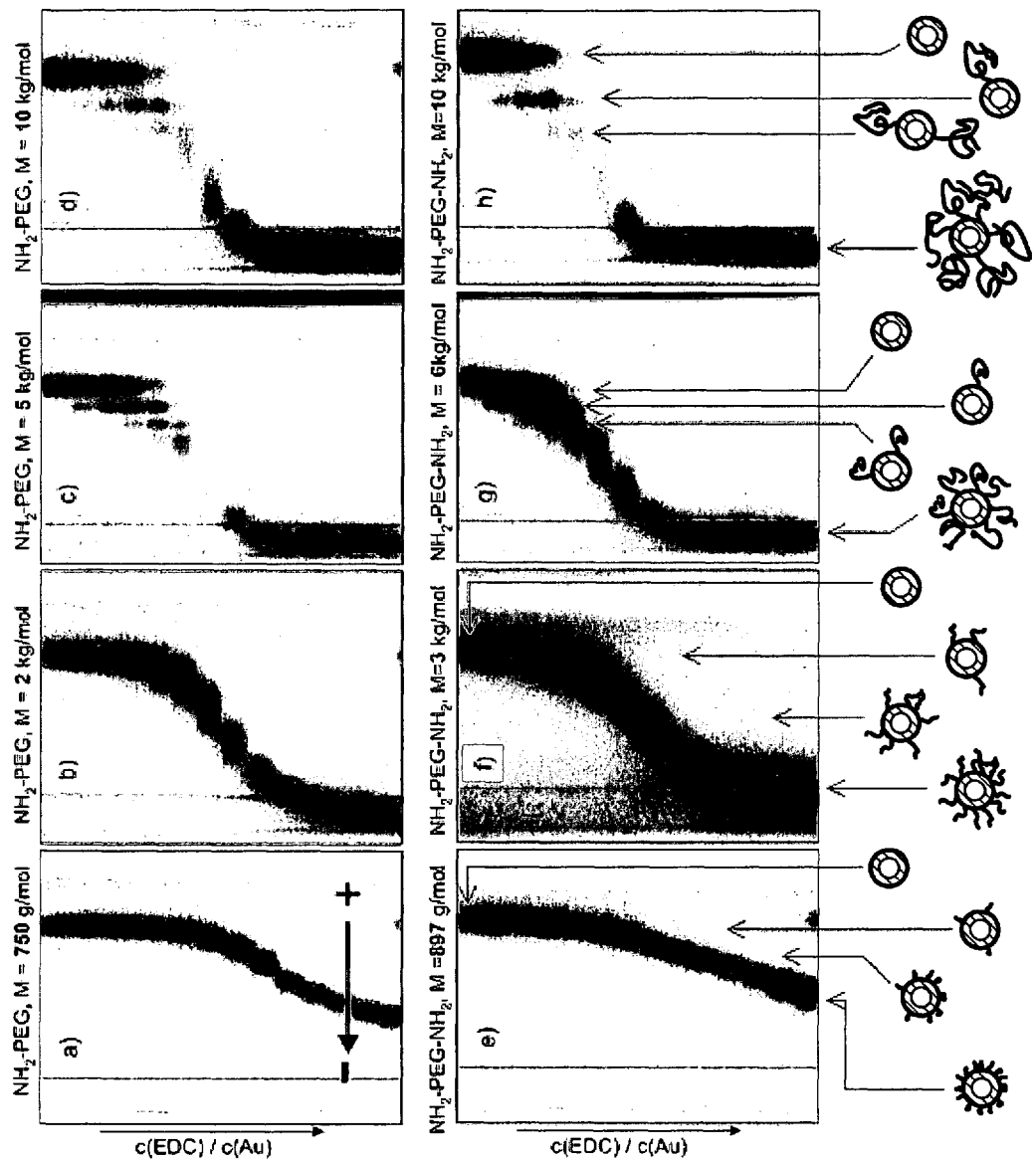
FIG. 4 is gel electrophoresis of PEG/Au conjugates. Different amino-modified PEG molecules were added to polymer-coated Au nanoparticles (core diameter ca. 4 nm): a) $NH_2$—PEG, molecular weight M=750 g/mol, b) $NH_2$—PEG, M=2000 g/mol, c) $NH_2$—PEG, M=5000 g/mol, d) $NH_2$—PEG, M=10000 g/mol, e) $NH_2$—PEG-$NH_2$, M=897 g/mol, f) $NH_2$—PEG-$NH_2$, M=3000 g/mol, g) $NH_2$—PEG-$NH_2$, M=6000 g/mol, h) $NH_2$—PEG-$NH_2$, M=10000 g/mol.

Length Dependence:

Gel electrophoresis of PEG/Au conjugates is shown in FIG. 4. Different amino-modified PEG functional ligands were added to polymer-coated Au nanoparticles (core diameter ca. 4 nm): a) $NH_2$—PEG, molecular weight M=750 g/mol, b) $NH_2$—PEG, M=2000 g/mol, c) $NH_2$—PEG, M=5000 g/mol, d) $NH_2$—PEG, M=10000 g/mol, e) $NH_2$—PEG-$NH_2$, M=897 g/mol, f) $NH_2$—PEG-$NH_2$, M=3000 g/mol, g) $NH_2$—PEG-$NH_2$, M=6000 g/mol, h) $NH_2$—PEG-$NH_2$, M=10000 g/mol. The PEG functional ligands (shown in curved lines) were attached via their $NH_2$-group to the COOH-groups of the polymer-shell of the Au nanoparticles (shown in white core with striped shell) with EDC. The amount of attached PEG functional ligands per Au nanoparticle was adjusted by changing the concentration of EDC in the following range: c(EDC)/c(Au-nanoparticle)=0, 31, 63, 125, 250, 500, 1000, 2000, 4000, 8000, 16000, 32000, 64000, 128000. After sufficient incubation time the reaction mixtures were loaded on a 2% agarose gel and run for 80-90 minutes. Due to their negative charge the conjugates migrate towards the plus pole. The first band (on the top of the gel) corresponds to the reaction mixture c(EDC)/c(Au)=0, the second one to c(EDC)/c(Au-nanoparticle)=31, etc. This means that the bands from the top to the bottom lane of each gel correspond to an increased number of PEG functional ligands attached per Au-nanoparticle. A dashed line marks the position on the gel where the conjugates have been loaded. The first lane of each gel corresponds to the reaction mixture to which no EDC has been added and thus no PEG has been attached to the nanoparticles. The more PEG is attached per nanoparticle the more the bands are retarded. At one point the nanoparticle surface is saturated with PEG and even the addition of more EDC does not result in an increase in size. This can be seen in the bands on the bottom of the gels, where the speed of migration does not decrease anymore upon the addition of more EDC. Even at saturation with PEG there are still enough free negatively charged —COOH groups available on the polymer surface (e.g. FIG. 4a). For PEG with high molecular weight discrete bands on the gel can be seen [see (c), (d), (g), (h) of FIG. 4]. We ascribe these bands to Au-nanoparticles with no, exactly one, and exactly two PEG functional ligands bound per nanoparticle. For PEG with low molecular weight no discrete bands can be observed and the number of bound PEG functional ligands per Au-nanoparticle cannot be resolved. In the case of saturation (for short and long PEG) the Au-nanoparticle surface is covered to the highest possible extent with PEG. However, the number of PEG functional ligands bound per nanoparticle can not be deduced from our data in this case.

For short $NH_2$—PEG functional ligands (molecular weight<5000 g/mol) the change in size due to the addition of one single PEG is too small to be detectable with gel electrophoresis. If more PEG is attached per nanoparticle the size of the conjugates gets continuously bigger and the bands on the gel are more retarded. At one point the nanoparticle surface is saturated with PEG, and the retardation of the nanoparticles on the gels remains constant [see (a) of FIG. 4]. The higher the molecular weight of the PEG is, the bigger the maximum retardation of the conjugates becomes [see (a)-(d) of FIG. 4]. At molecular weights 5000 g/mol the change upon binding of one PEG functional ligand to the nanoparticle surface yields a size change big enough to be detected as discrete band on the gel [see (c) and (d) of FIG. 4]. The higher the molecular weight of the PEG is, the bigger the retardation on the gel upon the addition of one single PEG becomes [see (c) and (d) of FIG. 4]. Upon saturation with long PEG the retardation of the conjugates even leads to a change in the direction of migration [see (b)-(d) of FIG. 4]. We speculate that this effect might be associated with the complexation of positively charged ions with the neutral PEG.

We have strong experimental evidence that, similar to DNA/Au nanoparticle conjugates, the main effect for retardation of the bands on the gel upon binding PEG to Au-nanoparticles is the change in the overall size: Upon attachment of each $NH_2$—PEG functional ligand via bond formation between the $NH_2$-group of the PEG and a COOH-group on the nanoparticle surface one negative charge on the nanoparticle surface (which originated from the COOH-group) is lost. This effect does not depend on the length of the PEG. However, since retardation on the gel was found to increase with the length of the PEG functional ligands, this retardation cannot be predominantly ascribed to the loss in negative charge, because this effect does not depend on the length of the PEG. For reasons of steric hindrance the maximum number of PEG functional ligands that can be attached per nanoparticle will decrease with the length of the PEG. Since in the case of saturation of nanoparticles with short PEG (i.e. in the situation when the maximum amount of PEG is attached per nanoparticle) the conjugates migrate towards the plus pole, we can conclude that even in the case of saturation PEG functional ligands have been only been attached to a fraction of the —COOH groups on the nanoparticle surface.

Introduction of Discrete Functional Groups:

$NH_2$—PEG-$NH_2$ of different molecular weight was attached with EDC to the polymer surface of Au-nanoparticles as described above for $NH_2$—PEG. Gel electrophoresis experiments demonstrated that the conjugates for Au-nanoparticles conjugated to $NH_2$—PEG-$NH_2$ and $NH_2$—PEG yield bands with comparable retardation on the gel [see (e)-(h) of FIG. 4]. This means that inter-particle crosslinking, which only would be possible in the case of $NH_2$—PEG-$NH_2$ if one PEG binds with both $NH_2$ groups to two different nanoparticles, can be neglected. In case of inter-particle crosslinking the bands for Au-nanoparticles conjugated to $NH_2$—PEG-$NH_2$ should be more retarded than the one for Au-nanoparticles conjugated to $NH_2$—PEG. As for the $NH_2$—PEG also for the $NH_2$—PEG-$NH_2$ with a molecular weight 5000 g/mol discrete bands could be observed with gel electrophoresis [see (g) and (h) of FIG. 4]. Since the bands can be ascribed to Au-nanoparticles with no, exactly one, exactly two, etc. PEG functional ligands per Au-nanoparticle these conjugates are in fact conjugates with a precisely controlled number of reactive groups on their surface. Whereas the polymer-surface of the Au-nanoparticles comprises only accessible —COOH groups, each attached $NH_2$—PEG-$NH_2$ bears one free —$NH_2$ group at its end that is pointing away from the nanoparticle. In this way conjugates with exactly one, two, etc. —$NH_2$ groups per nanoparticle are obtained.

Figure 5:
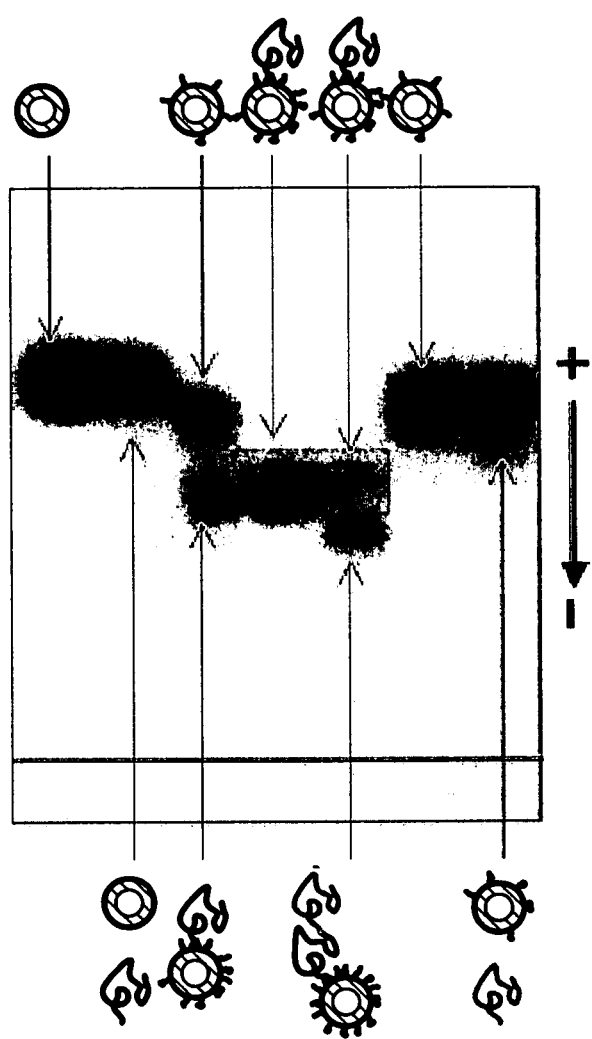
FIG. 5 shows addition of NHS-PEG-biotin to Au-nanoparticles with no $NH_2$-group or with exactly one $NH_2$-group per nanoparticle.

Stability of the Conjugates:

As mentioned above, the retardation of the conjugates that we ascribe to Au-nanoparticles with one and two bound PEG functional ligands increases with the length of the PEG. The formation of nonspecifically formed Au-nanoparticle clusters on the other hand should not depend on the length of the PEG. This fact strongly indicates that the discrete retarded bands cannot be ascribed to nonspecifically formed dimers and trimers of Au-nanoparticles. As further control we extracted the nanoparticles within the discrete bands from the gel and run the purified and re-concentrated sample again on a second gel (FIG. 5). Most of the extracted conjugates were found to migrate with the same speed as the original ones. Only a very weak band on the gel was found at the position of Au nanoparticles without PEG. This indicates that the conjugates are stable upon extraction from the gel, purification, and re-concentration, and that only for a minor fraction of the conjugates the PEG is removed from the nanoparticles.

Reactivity of the Discrete Functional Groups:

Referring to FIG. 5, polymer-coated Au nanoparticles were incubated with a 1:20 mixture of $NH_2$—PEG-$NH_2$ (molecular weight M=10000 g/mol) and $NH_2$—PEG (molecular weight M=750 g/mol) and the PEG was attached to the nanoparticles by adding EDC. Conjugates were run for 1 hour on a 2% agarose gel. In lane 1 the band of the pure Au nanoparticles and in lane 3 the two bands resulting from the PEG-Au conjugates are shown. We ascribe the faster band in lane 3 to Au nanoparticles to whose surface only some of the short $NH_2$—PEG have been attached. Due to these attached PEG the conjugates migrate slightly slower than the pure Au nanoparticles. The slower migrating band in lane 3 is ascribed to Au nanoparticles to which some short $NH_2$—PEG and exactly one long $NH_2$—PEG—$NH_2$ have been attached. The attachment of one single long $NH_2$—PEG-$NH_2$ is sufficient enough for a significant retardation (cfg. FIG. 4h). We have extracted the two bands from lane 3 from the gel and run them again together with the original sample. The fast migrating band of the extracted sample is shown in lane 6, and the slow migrating band of the extracted sample is shown in lane 4. The band in lane 4 migrates with the same speed as the slow band in lane 3 and the band in lane 6 migrates with the same speed as the fast band in lane 3. This demonstrates that conjugates can be stably extracted from the gel without breaking the bond between the PEG functional ligands and the Au-nanoparticles. We believe that the attached short $NH_2$—PEG functional ligands facilitate this stability. Conjugates without some short $NH_2$—PEG tended to aggregate during extraction from the gel and the following purification and concentration of the sample. We ascribe the more retarded band in lane 3 to Au nanoparticles with exactly one attached $NH_2$—PEG-$NH_2$ functional ligand (in addition to several short $NH_2$—PEG functional ligands). Therefore, each of these conjugates should possess exactly one reactive —$NH_2$ site (at the end of the PEG pointing towards solution). We tested this hypothesis by adding NHS-PEG-biotin (molecular weight M=5000 g/mol). The NHS group is reactive towards free $NH_2$ groups. Because of its height molecular weight the binding of NHS-PEG-biotin should be visible as further retardation on the gel. As control NHS-PEG-biotin was added to pure Au nanoparticles (see lane 2) and to Au nanoparticles with only short $NH_2$—PEG functional ligands attached (which have been extracted from the fast migrating band in lane 3, see lane 7). In both cases no shift can be seen and therefore we can rule out non-specific attachment of the NHS-PEG-biotin to the Au nanoparticles. However, when NHS-PEG-biotin was added to the conjugates bearing exactly one reactive $NH_2$-group (which have been extracted from the slow migrating band in lane 3) an additional band with enhanced retardation can be observed (see lane 5). The yield of this reaction is not 100%, since also a band at the position of the original conjugates remains. However, the existence of the more retarded band proves that the added NHS-PEG-biotin has been specifically attached to the original conjugates. This band corresponds to Au-nanoparticles with exactly one biotin-group per nanoparticle.

As described above we were able to synthesize conjugates of Au-nanoparticles with exactly one, two, etc. —$NH_2$ groups per nanoparticle. Using standard bioconjugation chemistry it should be possible to convert the —$NH_2$ groups to other functional groups or to attach biomolecules. We have demonstrated this possibility for the case of biotin by using NHS-modified biotin as biomolecule. Every biotin bearing an NHS group should be reactive towards the discrete —$NH_2$ groups of the conjugates. We have added NHS-PEG-biotin (5000 g/mol) to Au-nanoparticles with no or exactly one —$NH_2$ group per nanoparticle. As shown in FIG. 5, addition of NHS-PEG-biotin to Au-nanoparticles with no $NH_2$-group basically did not result in any shift on the gel and thus it can be derived that nonspecific adsorption of the PEG to the nanoparticles does not play a mayor role (FIG. 5, lanes 2 and 7). In the case of Au-nanoparticles with exactly one $NH_2$-group per nanoparticle the addition of NHS-PEG-biotin results in the formation of a second, more retarded band on the gel (FIG. 5, lane 5). This indicates that part of the Au-nanoparticles have reacted with the PEG, which in turn increased the size of the conjugates and thus reduced the mobility on the gel. This second band now corresponds to Au-nanoparticles with exactly one biotin-group per nanoparticle. However, besides the second retarded band, a band remains that has the same mobility as the original nanoparticles with one $NH_2$—PEG per nanoparticle. This means that in these experiment the yield in the conversion of the —$NH_2$ group to a-biotin group is not optimum.

Figure 6:
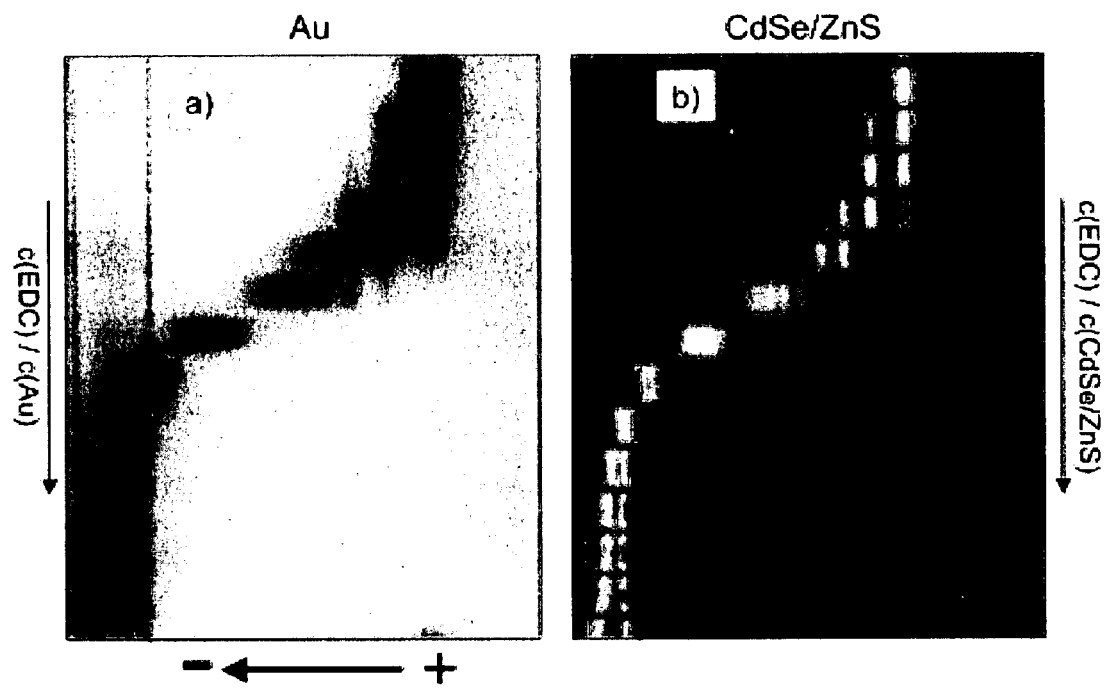
FIG. 6 is gel electrophoresis of PEG/Au and PEG/CdSe/ZnS conjugates.

Universality of the Concept:

Gel electrophoresis of PEG/Au and PEG/CdSe/ZnS conjugates is shown in FIG. 6. Amino-modified PEG functional ligands ($NH_2$—PEG, M=5000 g/mol) were added to polymer-coated Au nanoparticles (diameter of the Au core ca. 4 nm) (FIG. 6a) and CdSe/ZnS nanoparticles (diameter of the CdSe/ZnS core/shell ca. 7 nm) (FIG. 6b) and the number of attached PEG functional ligands per nanoparticle was adjusted by using different concentrations of EDC: c(EDC)/c(Au-nanoparticle) and c(EDC)/c(CdSe/ZnS-nanoparticle) =0, 31, 63, 125, 250, 500, 1000, 2000, 4000, 8000, 16000, 32000, 64000, 128000. These conjugates were run on a 2% agarose gel for 80-90 minutes and the lanes on the gel correspond to the different reaction mixtures, whereby the top lane corresponds to c(EDC)=0 and the bottom lane to the maximum EDC concentration. FIG. 6a is identical to FIG. 4c. By comparing FIGS. 6a and 6b it can be seen that the position of the bands on the gel does not depend on the nature of the inorganic nanoparticle material that is embedded in the polymer shell. In the case of Au nanoparticles discrete bands corresponding to conjugates in which exactly one, two, and three PEG functional ligands are attached per nanoparticle can be clearly resolved. In the case of the fluorescent CdSe/ZnS nanoparticles even bands of higher order (four and five PEG functional ligands per nanoparticle) can be resolved. This is due to the fact that the band of the pure CdSe/ZnS nanoparticles (i.e. without attached PEG functional ligands) is narrower than the band of the pure Au nanoparticles (top lane with c(EDC)=0 in both gels). However, for the pure CdSe/ZnS nanoparticles a weak second band can be observed. This band has to be attributed either to some non-specifically formed dimers of nanoparticles or to overloading the gel with nanoparticles. However, this second band is slightly less retarded than the band that we ascribe to CdSe/ZnS nanoparticles modified with on PEG (compare lanes 1 and 2 of FIG. 6b) and therefore does not interfere with the sorting process.

In previous work we have demonstrated that by embedding nanoparticles in a polymer shell we can synthesize nanoparticles of different materials (such as fluorescent or magnetic ones) that have an identical surface. For this reason also the concept of the attachment of individual functional ligands per nanoparticle is not restricted to one type of nanoparticles but should be applicable for nanoparticles of most materials. To demonstrate this generalization we have also conjugated fluorescent CdSe/ZnS-nanoparticles with individual $NH_2$—PEG functional ligands using the same protocols as have been applied for Au-nanoparticles. As shown in FIG. 6, PEG/Au— and CdSe/ZnS-nanoparticle conjugates show the same behavior upon gel electrophoresis, which demonstrates that the conjugation reaction does not depend on the properties of the inorganic nanoparticle inside the polymer shell. In a next step we tried to demonstrate that this concept should work also for different functional groups X. By conjugating polymer-coated Au-nanoparticles with NH$_2$—PEG-X functional ligands with PEG of sufficient length (molecular weight of the PEG 5000 g/mol) and running the conjugates on a gel discrete bands corresponding to nanoparticles with exactly no, one, two, etc. functional groups X per nanoparticle could be obtained. We have demonstrated this for the case of X=NH$_2$ and without X (see FIGS. 4g, h and 4c, d, respectively). Alternatively, by conjugating polymer-coated Au-nanoparticles with NH$_2$—PEG-NH$_2$ functional ligands of sufficient length (molecular weight of the PEG 5000 g/mol), running the conjugates on a gel and extracting the discrete bands from the gel conjugates corresponding to nanoparticles with exactly no, one, two, etc. NH$_2$-groups per nanoparticle were obtained. In a following step the discrete NH$_2$-groups could be converted to functional groups by reacting them with NHS—X. We have demonstrated this for the case of X=PEG-biotin (FIG. 5) reproduced the converting also with X=PEG-maleimide and X=PEG-BOC.

Figure 7:
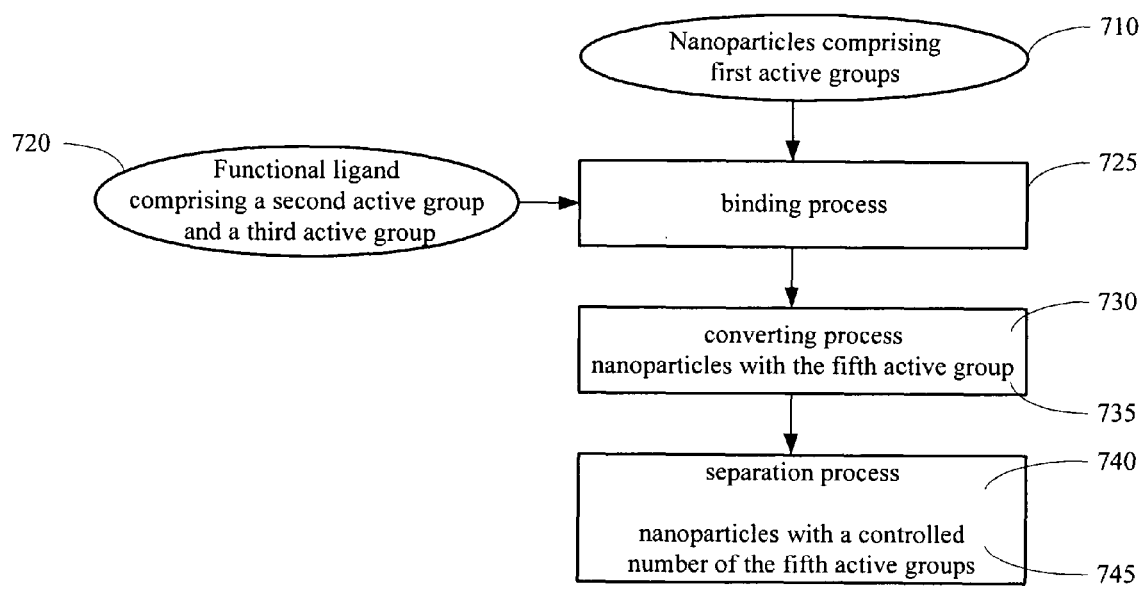
FIG. 7 is a flow chart of a method for separating nanoparticles with a controlled number of active groups in accordance with the second embodiment of the present invention.

Referring to FIG. 7, in a second embodiment of the present invention, a method for separating nanoparticles with a controlled number of active groups is disclosed. First, a plurality of nanoparticles 710 are provided, wherein the surface of the nanoparticle 710 comprises a plurality of first active groups. The preferred diameter of the nanoparticle 710, the material of the nanoparticle 710, and the preferred constructs of the nanoparticle 710 are described in the first embodiment. Next, a plurality of functional ligands 720 are provided, wherein the functional ligand 720 comprises at least one second active group and at least one third active group. The preferred constructs of the functional ligand 720 are described in the first embodiment. Then, a binding process 725 is performed to bind the nanoparticle 710 with the functional ligand 720, wherein the first active group connects with the second active group. After completion the binding process 725, a converting process 730 is performed to convert the third active group of the nanoparticle 710 into a fifth active group, so nanoparticles with the fifth active groups 735 are then formed. Finally, a separation process 740 is performed to isolate a plurality of nanoparticles with a controlled number of the fifth active groups 745, wherein the controlled number is integers from 0 to 10.

In this embodiment, the first active groups, the second active group, and the third active group are independently selected from the group consisting of:

a) chemical functional group, such as: sulfonic group, hydroxyl group, amino group, sulfhydryl group, carboxyl group, epoxy group, isocyanate group, organic halide group, maleimidyl group, alkoxy group, succinimidyl group, ortho-pyridylthiolic group, ortho-pyridyldisulfidyl group, vinylsulfonic group, acrylate group, alkyl ketone group, hydrazine group, hydrazide group, thioester group, and aldehydyl group.

b) biological molecule as described in definitions c) protecting group, such as: Fmoc group, Boc group In this embodiment, one example of the converting process 730 comprises: (1) providing a plurality of converters, wherein the converter comprises a fourth active group and at least one fifth active group; (2) connecting the third active group of the nanoparticle 710 with the fourth active group, so as to form a plurality of nanoparticles with the fifth active groups. Furthermore, the fourth active group and the fifth active group are independently selected from the group consisting of:

a) chemical functional group, such as: sulfonic group, hydroxyl group, amino group, sulfhydryl group, carboxyl group, epoxy group, isocyanate group, organic halide group, maleimidyl group, alkoxy group, succinimidyl group, ortho-pyridylthiolic group, ortho-pyridyldisulfidyl group, vinylsulfonic group, acrylate group, alkyl ketone group, hydrazine group, hydrazide group, thioester group, and aldehydyl group.

b) biological molecule as described in definitions c) protecting group, such as: Fmoc group, Boc group Another example of the converting process 730 comprises a redox reaction to reduce or oxidize the third active group to the fifth active group. Still another example of the converting process 730 comprises a deprotecting reaction. For a preferred case, the third active group is Fmoc-protected or Boc-protected amino group, and piperidine or TFA can be used as deprotecting agent respectively.

In this embodiment, the preferred molecular weight of the functional ligand is larger than or equal to 1000 g/mol, and the separation process comprises size exclusion chromatography (SEC) and gel electrophoresis, wherein SEC comprises Gel Chromatography. However, for nanoparticles with different size, different separation methods, different operational parameters (e.g. temperature, gel species), or different functional ligands, the molecular weight limit of the functional ligand might be varied. In a preferred example of this embodiment, 3000 g/mol is a better lower limit for the separation process.

In the above preferred embodiments, the present invention employs functional ligands, wherein the functional ligand can have at least one binding group and at least one active group. If the functional ligand(s) bound to a nanoparticle by the binding group change its overall effective size sufficiently enough, fractions of nanoparticles with a different number of functional ligands can be then separated. Therefore, nanoparticles with a controlled number of the active groups can be sorted out. The concept of the attachment of a defined number of functional ligands per nanoparticle is not restricted to one type of nanoparticles but should be applicable for nanoparticles of most materials, or shell types with functional groups, respectively. Therefore, this present invention does have the economic advantages for industrial applications. Therefore, this present invention does have the economic advantages for industrial applications.

To sum up, the present invention discloses a method for separating nanoparticles with a controlled number of active groups. First, a plurality of nanoparticles are provided, wherein the surface of the nanoparticle comprises a plurality of first active groups. Next, a plurality of functional ligands are provided, wherein the functional ligand comprises at least one second active group and at least one third active group. Then, a binding process is performed to bind the nanoparticle with the functional ligand, wherein the first active group connects with the second active group. After the binding process, a separation process is performed to isolate a plurality of nanoparticles with a controlled number of the third active groups. The controlled number is integers from 0 to 10.

Obviously many modifications and variations are possible in light of the methods described above. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for separating nanoparticles with a controlled number of active groups, comprising:
   providing a plurality of nanoparticles, wherein the surface of said nanoparticles comprises a plurality of first active groups;
   performing a modification process to modify the surface of said nanoparticles with said first active groups by an amphiphilic oligomer or polymer which has at least one —COOH group to form polymer coated nanoparticles with said first active groups;
   providing a plurality of functional ligands, wherein the molecular weight of said functional ligands is larger than 3000 g/mol, and said functional ligands comprises at least one second active group and at least one third active group, wherein said functional ligands further comprises a spacer, wherein said spacer comprises polyethylene glycol which has at least one —NH2 group;
   performing a binding process to bind said polymer coated nanoparticles and said functional ligands together through the connection between said first active groups of said polymer coated nanoparticles and said second active group of said functional ligands by controlling the concentration ratio of the polymer coated nanoparticles to the functional ligands to form polymer coated nanoparticles with a controlled number of functional ligands; and
   performing a separation process selected from one of the following group: size exclusion chromatography (SEC) and gel electrophoresis to isolate a plurality of polymer coated nanoparticles with a predetermined number of said third active groups from said polymer coated nanoparticles with a controlled number of functional ligand wherein the controlled number ranges from 0 to 10 and the predetermined number is an integer selected from 1 to 10.

2. The method as claimed in claim 1, wherein the diameter of said nanoparticle is smaller than 50 nm.

3. The method as claimed in claim 1, wherein the nanoparticle is selected from a group consisting of quantum dot, metallic nanoparticle, and metal oxide nanoparticle.

4. The method as claimed in claim 1, wherein said nanoparticle has said plurality of first active groups thereon.

5. The method as claimed in claim 1, wherein said spacer is bound with said second active group and said third active group.

6. The method as claimed in claim 1, wherein said spacer has said third active group therein, and bound with said second active group.

7. The method as claimed in claim 1, wherein said spacer has said second active group and said third active group therein.

8. The method as claimed in claim 1, wherein said first active groups, said second active group, and said third active group are independently selected from a group consisting of:
   a) chemical functional group;
   b) biological molecule; and
   c) protecting group.

9. The method as claimed in claim 1, wherein the connecting type between said first active group and said second active group is chemical bonding or physical bonding.

10. The method as claimed in claim 1, further comprising a converting process, after said separation process, to convert said third active group of said polymer coated nanoparticles into a fifth active group.

11. The method as claimed in claim 10, wherein said converting process comprises:
   providing a plurality of converters, wherein said converter comprises a fourth active group and at least one fifth active group; and
   connecting said third active group of said polymer coated nanoparticles with said fourth active group, so as to form a plurality of polymer coated nanoparticles with a controlled number of said fifth active groups.

12. The method as claimed in claim 11, wherein said fourth active group and said fifth active group are independently selected from a group consisting of:
   a) chemical functional group;
   b) biological molecule; and
   c) protecting group.

13. The method as claimed in claim 1, wherein said functional ligand further comprises at least one cleaving site between said second active group and said third active group.

14. The method as claimed in claim 13, wherein said cleaving site comprises one of the following group: disulfide bond, peptide, protein, DNA, RNA and PNA.

15. The method as claimed in claim 13, further comprising a cleaving process after said separation process, so as to break said cleaving site to form a sixth active group.

16. The method as claimed in claim 15, wherein said cleaving process uses a cleaving agent comprising one of the following group: reduction agent, trypsin, and enzymes.

17. The method as claimed in claim 13, wherein said functional ligand further comprises a seventh active group between said second active group and said cleaving site.

* * * * *